US00PP28742P3

(12) United States Plant Patent
Giesen

(10) Patent No.: US PP28,742 P3
(45) Date of Patent: Dec. 5, 2017

(54) ***DAHLIA* PLANT NAMED 'DAHZ0014'**

(50) Latin Name: ***Dahlia* hybrid Cav.**
Varietal Denomination: DAHZ0014

(71) Applicant: SYNGENTA PARTICIPATIONS AG, Basel (CH)

(72) Inventor: Eric Giesen, Andijk (NL)

(73) Assignee: Syngenta Participations AG, Basel (CH)

( * ) Notice: Subject to any disclaimer, the term of this patent is extended or adjusted under 35 U.S.C. 154(b) by 102 days.

(21) Appl. No.: 14/757,249

(22) Filed: Dec. 10, 2015

(65) Prior Publication Data

US 2016/0205856 P1 Jul. 14, 2016

Related U.S. Application Data

(60) Provisional application No. 62/102,271, filed on Jan. 12, 2015.

(51) Int. Cl.
*A01H 5/02* (2006.01)

(52) U.S. Cl.
USPC ..... Plt./321

(58) Field of Classification Search
USPC ..... Plt./263.1, 321
See application file for complete search history.

*Primary Examiner* — Susan McCormick Ewoldt
*Assistant Examiner* — Karen Redden
(74) *Attorney, Agent, or Firm* — Dale Skalla

(57) ABSTRACT

A new *Dahlia* plant named 'DAHZ0014', particularly distinguished by scarlet-rose bi-color double flowers, compact and upright plant habit with good branching, medium green foliage, and good floriferousness.

1 Drawing Sheet

Latin name of the genus and species of the plant claimed: *Dahlia* hybrid Cav.

Varietal denomination: 'DAHZ0014'.

BACKGROUND OF THE NEW PLANT

The present invention comprises a new *Dahlia*, botanically known as *Dahlia* hybrid and hereinafter referred to by the variety name 'DAHZ0014'.

'DAHZ0014' is a product of a planned breeding program. The new cultivar has scarlet rose bi-color double flowers, compact and upright plant habit with good branching, medium green foliage, and good floriferousness.

'DAHZ0014' originates from a sibling cross hybridization in a controlled breeding program in Andijk, Netherlands. The pollinations were made Andijk, Netherlands in May 2008.

The female parent was an unpatented, proprietary hybrid seedling identified as 'D08-69-16', having red-rose bi-color flower color, dark green foliage and a more compact plant habit than 'DAHZ0014'.

The male parent of 'DAHZ0014' was an unpatented, proprietary plant identified as 'D07-310' with bronze-white bi-color flower color, medium flower size, light green leaves, and not good branching plant habit.

The resulting the seed sown in May 2009, and 'DAHZ0014' was selected as one flowering plant within the progeny of the stated cross in September 2009 in a greenhouse in Andijk, Netherlands.

The first act of asexual reproduction of 'DAHZ0014' was accomplished when vegetative cuttings were propagated from the initial selection in October 2009 in a controlled environment in Andijk, Netherlands.

BRIEF SUMMARY OF INVENTION

Horticultural examination of plants grown from cuttings of the plant initiated in April 2012 in Andijk, Netherlands, and continuing thereafter, has demonstrated that the combination of characteristics as herein disclosed for 'DAHZ0014' are firmly fixed and are retained through successive generations of asexual reproduction.

'DAHZ0014' has not been observed under all possible environmental conditions. The phenotype may vary significantly with variations in environment such as temperature, light intensity and day length.

A Plant Breeder's Right for this cultivar was applied for in the European Community Plant Variety Office (CPVO) on May 5, 2014, No. 2014/1210. 'DAHZ0014' has not been made publicly available more than one year prior to the filing of this application.

The following traits have been repeatedly observed and are determined to be basic characteristics of the new variety. The combination of these characteristics distinguishes this *Dahlia* as a new and distinct variety.

BRIEF DESCRIPTION OF THE PHOTOGRAPHS

Figure 1:
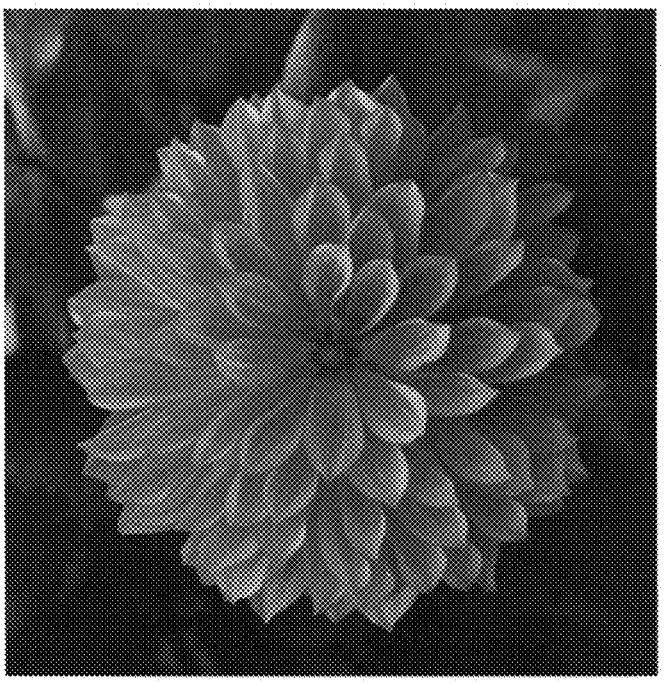
Figure 2:
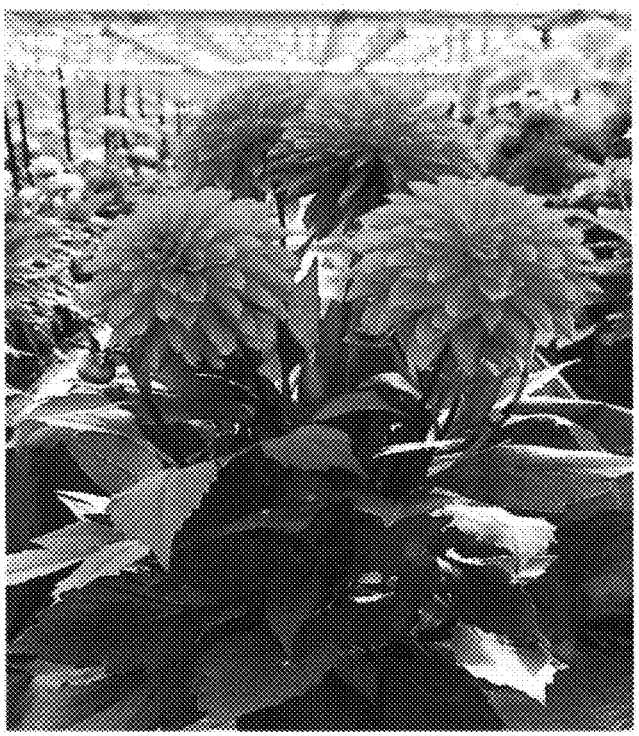

The accompanying photographic drawings show typical flower and foliage characteristics of 'DAHZ0014' with colors being as true as possible with an illustration of this type. The photographic drawings show in FIG. 1, a close-up of the flowers and in FIG. 2, a flowering potted plant of the new variety.

DETAILED BOTANICAL DESCRIPTION

The aforementioned photographs were taken in May 2013 in Andijk, Netherlands. The plants were growing in 13 cm pots on benches in a greenhouse. They were about 14 weeks of age The plant descriptions and measurements were taken in Enkhuizen, The Netherlands on Sep. 4, 2014, from 14 week old plants that were growing outdoors in the trial field.

Color references are made to The Royal Horticultural Society Colour Chart (R.H.S.) 2001.

TABLE 1

DIFFERENCES BETWEEN THE NEW VARIETY 'DAHZ0014' AND A SIMILAR VARIETY

| | 'DAHZ0014' | 'Hypnotica Rose Bicolor' |
|---|---|---|
| Overall flower color: | Scarlet-Rose bi-color | Pink-White bi-color |
| Flower type or position: | Semi Double flower | Full double flower |
| Foliage: | Medium green leafs | Dark green leafs |
| Plant size or habit: | Medium large plant with open plant habit | Large plant with compact dense plant habit |

Plant:

*Form, growth and habit.*—Semi-upright, tight and compact; freely branching.

*Plant height.*—30 cm.

*Plant height (inflorescence included).*—39 cm.

*Plant width.*—42 cm.

*Garden performance and tolerance to weather.*—Good.

*Crop time to flowering.*—About 9-12 weeks.

Roots:

*Number of days to initiate and develop roots.*—About 21-28 days at about 21 degrees C.

*Type.*—Fine, fibrous, free branching.

*Color.*—RES N155A.

Foliage:

*Arrangement.*—Opposite, single, simple and sometimes pinnate.

*Immature, leaf color, upper surface.*—RHS 136B.

*Lower surface.*—RHS 138B to RHS 138C.

*Mature, leaf color, upper surface.*—RHS 147B.

*Lower surface.*—RHS 146B.

*Type.*—Mostly simple, some are pinnate.

*Length.*—12 cm, including petiole.

*Width.*—9-10 cm.

*Shape.*—Ovate to deltoid for the pinnate Base shape: Pinnate leaves are truncate, simple leaves are acute.

*Apex shape.*—Acute to obtuse.

*Margin.*—Dentate.

*Texture, upper surface.*—Little hairy on the edges, slightly glossy.

*Lower surface.*—Some lonely hair on the main vein.

*Venation color, upper.*—RHS 144B.

*Lower.*—RHS 144D.

*Petiole color.*—RHS 144C.

*Petiole length.*—1-4 cm.

*Diameter of petiole.*—0.3 cm at the mid-section.

*Texture.*—Glabrous.

Stem:

*Average quantity of main branches per plant.*—About 5 to 6, each divides into 3 secondary branches.

*Color of stem.*—RHS 144B.

*Length of stem.*—25 cm.

*Diameter.*—0.6 cm at the midsection.

*Length of internodes.*—5.5-8.5 cm.

*Texture.*—Glabrous.

*Color of peduncle.*—RHS N144D.

*Length of peduncle.*—6-10 cm.

*Peduncle diameter.*—0.2-0.3 cm.

*Texture.*—Glabrous.

Inflorescence:

*Type.*—Inflorescences borne on terminals above foliage; daisy-eyed double.

*Blooming habit.*—Continuous throughout the growing season.

*Average quantity of inflorescences per plant.*—75, with buds.

*Average quantity of inflorescences per lateral stem.*—10-13.

*Lastingness of individual blooms on the plant.*—7-12 days.

*Fragrance.*—None.

Bud (just before opening):

*Color.*—RHS 58C on the top, to greener at the base: RHS 144B.

*Length.*—1.6 cm.

*Width.*—1.8 cm.

*Shape.*—Completely round to bell-shaped with unfolding of the rays.

Immature Inflorescence:

*Diameter.*—About 6.5 cm.

*Color of ray florets, upper surface.*—RHS N57A.

*Lower surface.*—RHS 58A.

Mature Inflorescence:

*Diameter.*—8.5-10 cm.

*Depth.*—4 cm.

*Total diameter of 'disc'.*—1.2 -1.4 cm.

*Recepticle height.*—0.2 cm.

*Recepticle diameter.*—1.4-1.5 cm.

Ray florets:

*Average quantity of florets.*—About 70, disposed in few layers.

*Color of florets, upper surface.*—RHS N57D.

*Lower surface.*—RHS 58C.

*Length.*—3.0-3.2 cm.

*Width.*—1.5 cm.

*Shape.*—Broadly elliptical.

*Base shape.*—Rolled to fused just at the base, acute.

*Apex shape.*—Mucronulate.

*Margin.*—Entire.

*Texture, upper surface.*—Papillose; glabrous.

*Lower surface.*—Papillose; some lonely hair on the veins.

*Number of petaloids.*—2-3 per ray floret.

*Color of petaloids, upper surface.*—As the petals, deeper than RHS 57D.

*Lower surface.*—RHS N57A.

*Length.*—0.5-1 cm.

*Width.*—0.2-0.4 cm.

*Shape.*—Strongly involute and sometimes twisted.

*Apex shape.*—Rounded to acute.

Disc florets:

*Average quantity of florets.*—About 70-75 quantity.

*Color of florets.*—RHS N57D.

*Length.*—0.6-0.9 cm.

*Width.*—0.25 cm.

*Shape.*—Tube-shaped.

*Apex shape.*—Acute, 5-pointed.

Phyllaries:

*Types of phyllaries 2 types.*—Phyllaries are arranged in 2-3 whorls.

*Phyllaries of lower whorl are green and thicker.*—

*Average quantity.*—About 5-7.

*Color, upper surface*.—RHS 146B.
*Lower surface*.—RHS 146A.
*Length*.—1.0 cm.
*Width*.—0.6 cm.
*Shape*.—Ovate.
*Base shape*.—Shortly attenuate.
*Apex shape*.—Acuminate.
*Margins*.—Entire.
*Texture, upper surface*.—Glabrous (no hair).
*Lower surface*.—Glabrous.
*Phyllaries in the upper whorl are mostly transparent*.—
*Average quantity*.—About 10.
*Color, upper surface*.—RHS 154A to RHS 154B.
*Lower surface*.—RHS 154B to RHS 154C.
*Length*.—1.6 cm.
*Width*.—0.6 cm.
*Shape*.—Ligulate.
*Base shape*.—Fused.
*Apex shape*.—Obtuse.
*Margins*.—Entire.
*Texture, upper surface*.—Glabrous (no hair).
*Lower surface*.—Glabrous.

Reproductive organs:
*Gyneocium*.—Present on both ray and disc.
*Pistil quantity*.—1 per floret.
*Length*.—0.8-0.9 cm.
*Style color*.—RHS 155A.
*Style length*.—0.5-0.6 cm.
*Stigma color*.—RHS 12A.
*Stigma shape*.—Bi-furchate (bi-lobed).
*Ovary color*.—RHS 145A.
*Andreocium*.—Present on disc florets only.
*Stamens quantity*.—5 united.
*Color of filaments*.—RHS 150A.
*Length filaments*.—0.3 cm.
*Anther color*.—RHS 16A.
*Anther length*.—0.4 cm.
*Color of pollen*.—RHS 16A.
*Pollen amount*.—Very moderate.
*Fertility/seed set*.—Not observed on this hybrid.

What is claimed is:

1. A new and distinct variety of *Dahlia* plant named 'DAHZ0014', substantially as illustrated and described herein.

* * * * *